(12) United States Patent
Yin et al.

(10) Patent No.: US 11,123,062 B2
(45) Date of Patent: Sep. 21, 2021

(54) SURGICAL METHOD FOR RECONSTRUCTING LABIONASAL MUSCLE TENSION STRUCTURE

(71) Applicant: Hospital of Plastic Surgery, Chinese Academy of Medical Sciences, Beijing (CN)

(72) Inventors: Ningbei Yin, Beijing (CN); Haidong Li, Beijing (CN); Yongqian Wang, Beijing (CN); Tao Song, Beijing (CN); Di Wu, Beijing (CN)

(73) Assignee: Hospital of Plastic Surgery, Chinese Academy of Medical Sciences, Beijing (CN)

( * ) Notice: Subject to any disclaimer, the term of this patent is extended or adjusted under 35 U.S.C. 154(b) by 317 days.

(21) Appl. No.: 16/522,679

(22) Filed: Jul. 26, 2019

(65) Prior Publication Data
US 2021/0022727 A1    Jan. 28, 2021

(51) Int. Cl.
*A61B 17/04*    (2006.01)
*A61B 17/00*    (2006.01)
*A61F 2/00*    (2006.01)

(52) U.S. Cl.
CPC .... *A61B 17/0469* (2013.01); *A61B 2017/00747* (2013.01); *A61B 2017/00792* (2013.01); *A61F 2/0059* (2013.01)

(58) Field of Classification Search
None
See application file for complete search history.

(56) References Cited

U.S. PATENT DOCUMENTS

| | | | | |
|---|---|---|---|---|
| 8,857,442 | B1* | 10/2014 | Ospina | A61B 18/20 128/898 |
| 2003/0120307 | A1* | 6/2003 | Abergel | A61F 2/0095 606/207 |
| 2004/0176856 | A1* | 9/2004 | Raphael | A61F 2/02 623/23.72 |
| 2006/0161253 | A1* | 7/2006 | Lesh | A61M 29/02 623/8 |

(Continued)

FOREIGN PATENT DOCUMENTS

RU    2110967 C1 *    5/1998

OTHER PUBLICATIONS

Espacenet English language machine translation of RU2110967C1 (Year: 1998).*
STIC EIC3700 NPL search for instant application (Year: 2021).*

*Primary Examiner* — Shaun L David (57) ABSTRACT

The technical problem to be solved by the present invention is to design a cosmetic surgical method for presenting a deeper or longer philtrum at the lip by adjusting the muscle flaps at the lips and nose. The theoretical basis of this surgical method is a "theory of labionasal muscle tension thread group" summarized from a series of studies with respect to anatomy, biomechanics and clinical surgical verification. According to this theory, the labionasal muscle tension structure is reconstructed by surgical adjustment of the position and direction of the muscle flaps, so as to produce an effect of changing the profile of the "philtrum" and to improve or remodel the "philtrum" as an aesthetic labial structure.

5 Claims, 11 Drawing Sheets
(11 of 11 Drawing Sheet(s) Filed in Color)

(56) References Cited

U.S. PATENT DOCUMENTS

| | | | |
|---|---|---|---|
| 2007/0098755 A1* | 5/2007 | Patel | A61F 2/0059 424/423 |
| 2007/0173887 A1* | 7/2007 | Sasaki | A61B 17/0401 606/232 |
| 2011/0093088 A1* | 4/2011 | Chen | A61F 2/0059 623/23.72 |

* cited by examiner

SURGICAL METHOD FOR RECONSTRUCTING LABIONASAL MUSCLE TENSION STRUCTURE

TECHNICAL FIELD

The present invention belongs to the technical field of plastic surgery, and in particular relates to a surgical method for reconstructing a labionasal muscle tension structure.

BACKGROUND

Muscles still have some tension their relaxed state, and this mechanical stress functions to help maintain the posture of the torso and to provide necessary background tension for muscle movement. On the same principle, when the lips are at rest, their appearance is maintained by the tension of the orbicularis oris and peripheral assisting muscles. Moreover, such muscle tension is symmetrical on both sides of the face, making the face keep symmetrical during development.

The morphology of human organs is not just formed due to stacking of simple tissues. The superficial muscle fascia system itself has an intrinsic biomechanical balance, and the morphology of body surface organs such as the lips and nose s actually an expression form of this balance on the body surface. Therefore, the shape of the lips and nose is also not completely determined by the volume of the soft tissue itself, but in fact maintained by muscle tension, and its formation results from the action of relevant muscles during the growth and development. Although recent literature has shown that people start to pay attention to fixation or over-and-out suturing at different positions of muscles in a lip surgery, their idea still remains at the level of morphological construction by means of tissue accumulation of muscles per se, and has not formulated a theory from the point of view of the biomechanical effect of muscles, that is, the muscle tension.

Figure 1:
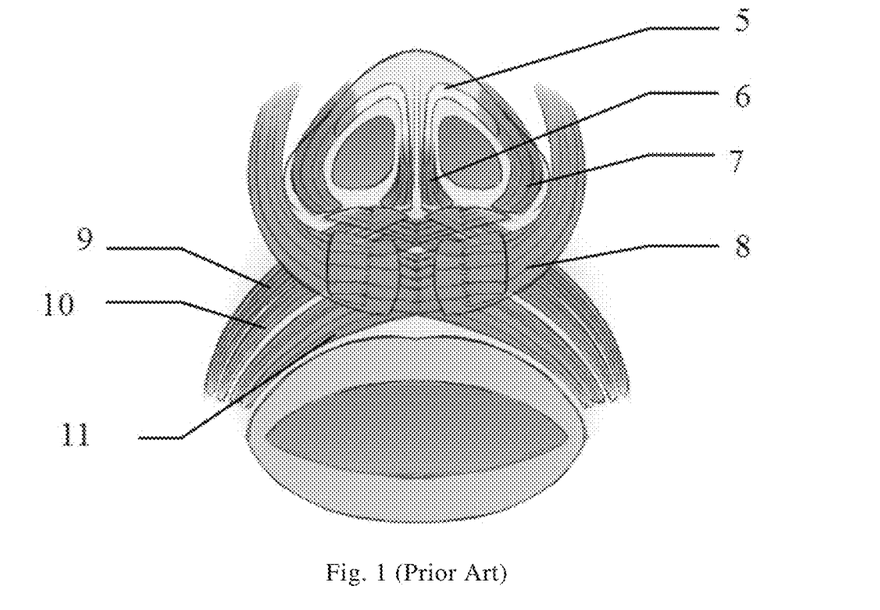
FIG. 1 is a schematic diagram of an anatomical structure of upper-lip muscles.

Studies have shown that the labionasal muscles have delicate and complex anatomical structures (FIG. 1). The orbicularis oris muscle of the upper lip is not of a simple ring structure, but has three branches on each of the left and right sides (numbered as the A1 branch of orbicularis oris, the A2 branch of orbicularis oris, and the A3 branch of orbicularis oris). These three branches start from the angle oris, and end at the anterior nasal spine, at the opposite nasal floor, and at the outer edge of the philtrum ridge on the opposite side, respectively. Meanwhile, the levator labii superioris alaeque nasi on each of the left and right sides also has three branches (numbered as levator labii superioris alaeque nasi B1, levator labii superioris alaeque nasi B2, and levator labii superioris alaeque nasi B3), starting from the medial angle of eyes, travelling along the outer edge of the back of nose, and extending beyond the nasal ala. Among them, the B1 branch of levator labii superioris alaeque nasi bypasses the outside of the nasal ala, and ends at the inner margin of a philtrum ridge, while the B2 and B3 branches of levator labii superioris alaeque nasi keep travelling down and end at the labial peaks and the outer edge of the labial arch. The surgical method described in the present application does not involve the B2 and B3 branches of levator labii superioris alaeque nasi, which are therefore omitted in the figures for convenience.

When two of these muscles meet each other during their travelling, their muscle fibers are interlaced at cross points, so that their muscle tensions would affect each other at the cross points, which correspondingly produces an influence on the surface morphology of the lips and nose. According to the cross points, the tension of each muscle is divided into three groups: i) the primary tension thread group (FIG. 2), in which the cross point is at the center of the upper lip and functions to maintain the morphological symmetry of the upper lip and nose; ii) the first secondary tension thread group (FIG. 3), in which the cross points are at the nasal floor on both sides, and which forms a ribbon-like tension transmission path by means of the connection of the nasal alar cartilage to the depressor septi nasi and the dilator naris muscle, functioning to maintain the morphology of nostrils; iii) the second secondary tension thread group (FIG. 4), in which the cross points are under the skin of the philtrum ridges on both sides, and which functions to form the special morphology of the philtrum having a central dimple and two ridgy edges. The surgical method described in the present application mainly relates to the second secondary tension thread group.

Under the long-term action of muscle tension, the nostril width, the convexity of the nasal ala, the involution of the root of nasal ala, the eight of lip peak, the symmetry of lips and nose, and the like are maintained. Changes in muscle tension can lead to changes in these morphologies. Therefore, cosmetic correction and deformity repair (i.e., morphological changes) of lips and nose can be achieved by adjustment of muscle tension to reach a new balance. It is thus required, according to the anatomical structure of muscles, to divide the muscles of the lips and nose into different muscle flaps, and to reestablish the stereoscopic relationship between muscles, such as their crossing, overlapping, and relative antagonism, according to a morphology we expect.

SUMMARY

The technical problem to be solved by the present invention is to design a cosmetic surgical method for presenting a deeper or longer philtrum at the lip by adjusting the muscle flaps at the lips and nose. The theoretical basis of this surgical method is a "theory of labionasal muscle tension thread group" summarized from a series of studies with respect to anatomy, biomechanics and clinical surgical verification. According to this theory, the labionasal muscle tension structure is reconstructed by surgical adjustment of the position and direction of the muscle flaps, so as to produce an effect of changing the morphology of the "philtrum" and to improve or remodel the "philtrum" as an aesthetic labial structure.

In order to achieve the above objective, the technical solution adopted by the present invention is a surgical method for reconstructing a labionasal muscle tension structure, comprising the steps of:

1) incision: making incisions at vermilion mucosa and at the bottom of the nasal column;

2) formation of muscle flaps: detaching a muscle layer in the incision the skin and the vermilion mucosa, and cutting open the detached muscle layer both longitudinally at the positions corresponding to philtrum ridges and transversely at about ¼ from the top, to obtain four muscle flaps which are respectively a depressor septi nasi flap, a dilator naris muscle flap, a medial orbicularis oris flap, and a lateral orbicularis oris flap;

3) adjustment of muscle flaps: fixing the tip of the dilator naris muscle flap to the anterior nasal spine, fixing the tip of the depressor septi nasi flap to the tail end of the dilator naris muscle flap, and then cross-stitching the lateral orbicularis oris flap and the medial orbicularis oris flap to deepen and/or lengthen the philtrum;

4) suturing: after the muscle flaps are treated, suturing the two incisions at the vermilion mucosa and the bottom of the nasal column as they were.

On the basis of the above technical solution, the present invention can u her comprise the following specific choices or preferred choices.

Specifically, in the step of detaching the muscle layer in the incision from the skin and the vermilion mucosa, when the philtrum is to be deepened, the muscle located from the upper lip midline to the bottom of the nasal column is not separated from the skin; when the philtrum is to be lengthened, the muscle at the bottom of the nasal column is separated from the skin, while the subcutaneous portion of the upper lip midline is not separated.

Specifically, the deepening the philtrum comprises: lifting the tip of the lateral orbicularis oris flap inwards and upwards, and fixing the tip to the tail end of the depressor septi nasi flap; suturing the right edge of the medial orbicularis oris flap toward the deep side of the lateral orbicularis oris flap, such that the right edge of the medial orbicularis oris flap substantially extends in the direction of a philtrum ridge; and suturing the left edge of the lateral orbicularis oris flap under the skin of the philtrum dimple, such that the left edge of the lateral orbicularis oris flap substantially extends in the direction of a philtrum ridge.

Alternatively, lengthening the philtrum comprises: lifting the tip of the lateral orbicularis oris flap inwards and upwards, and fixing the tip to the anterior nasal spine; and suturing the right edge of the medial orbicularis oris flap toward the deep side of the lateral orbicularis oris flap, and suturing the left edge of the lateral orbicularis oris flap under the skin of the philtrum dimple, such that when the suturing the lateral orbicularis oris flap is sutured relatively high and the medial orbicularis oris flap is relatively low, and the height difference between the lateral orbicularis oris flap and the medial orbicularis oris flap makes the philtrum lengthened.

The above-mentioned surgical method for reconstructing a labionasal muscle tension structure can achieve better cosmetic and deformity-repairing effects of deepening the philtrum and lengthening the upper lip with less damage. According to the running directions of the muscle fibers of muscles at the lips and nose, their muscle flaps are divided (i.e., the depressor septi nasi flap, the dilator naris muscle flap, the medial orbicularis oris flap, and the lateral orbicularis oris flap) and serve to bear and transmit the corresponding muscle tension, and finally reconstruct the labionasal muscle tension structure.

The operations, such as fixing the tip of the dilator naris muscle flap to the anterior nasal spine, overlaying the dilator naris muscle flap with the inverted depressor septi nasi flap, and tightening the lateral orbicularis oris flap inwards and upwards, adjust the muscle attachment points to optimal positions, so as to connect the skin of the lips and change the surface morphology of the lips. The two muscle flaps under a philtrum ridge are superimposed over each other, with their respective tension threads crossed, drawing the skin areas flanking the philtrum ridge towards the middle, thereby elevating the philtrum ridge. The attachment point of the lateral orbicularis oris flap is moved downwards, which changes the tension lifting the upper lip and thus lengthens the philtrum.

The spirit of the invention is in two folds:
1. The muscles are divided into four main muscle flaps according to the different tensions they bear;
2. The four muscle flaps are re-fixed to new attachment points according to needs.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

In the drawings, parts indicated by various reference numbers are listed as follows:

1, Depressor septi nasi flap; 2, Dilator naris muscle flap; 3, Medial orbicularis oris flap; 4, Lateral orbicularis oris flap; 5, Nasal alar cartilage; 6, Depressor septi nasi; 7, Dilator naris muscle; 8, Levator labii superioris alaeque nasi; 9, A1 branch of orbicularis oris; 10, A2 branch of orbicularis oris; 11, A3 branch of orbicularis oris.

DETAILED DESCRIPTION

For a better understanding of the present invention, the content of the present invention will be further described with reference to drawings and specific examples, but is not only limited to the following examples.

Figure 2:
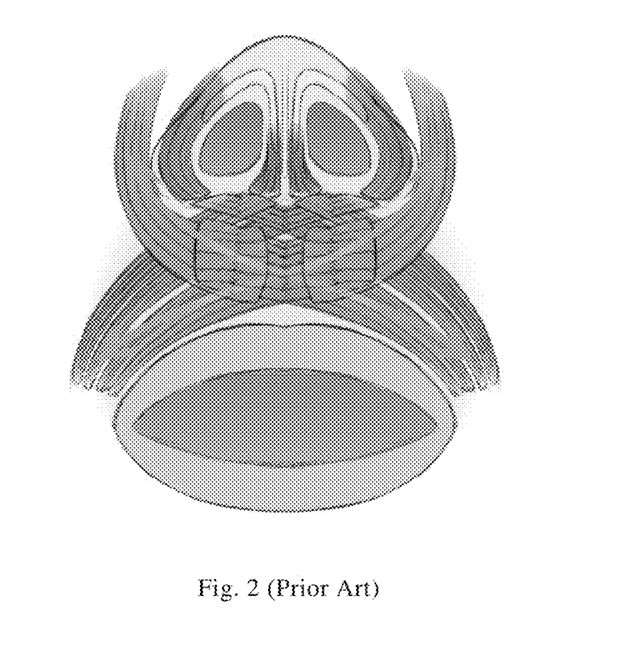
FIG. 2 is a schematic diagram of a primary tension thread group.

Among them, the upper labionasal muscles in FIG. 2 have a plurality of intersecting structures, and the sum of their tensions results in, at the center of the upper lip, a combined force with its components on left and right sides counteracting each other, thereby maintaining the morphological balance between both sides of the upper lip and nose.

Figure 3:
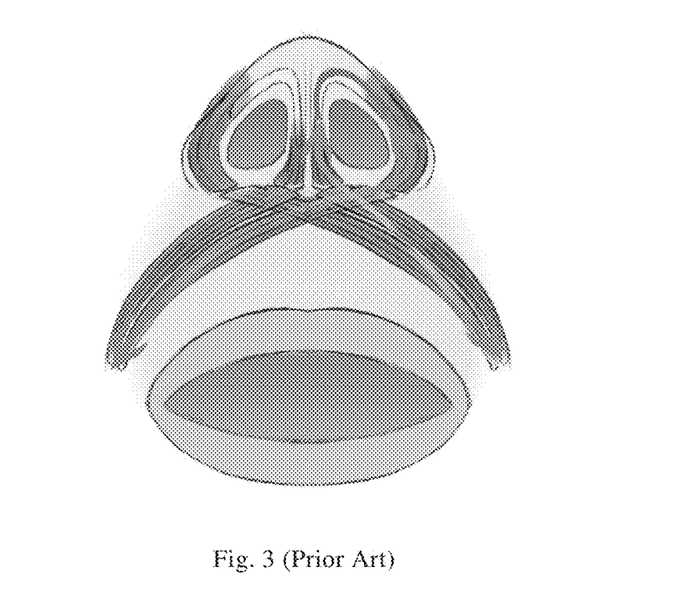
FIG. 3 is a schematic diagram of a first secondary tension thread group.

In FIG. 3, the first secondary tension thread group includes two tension threads that are bilaterally symmetrical. Take the left side as an example: the A1 branch of orbicularis oris on the left side starts from the left angle oris, travels to the vicinity of the anterior nasal spine, and joins with the left depressor septi nasi. At the same time, the A2 branch of orbicularis oris on the right side starts from the right angle oris, travels to the left nasal floor, and joins with the left dilator naris muscle. During its travelling, it interests the A1 branch of orbicularis oris on the left side at the left nasal floor. The tension of these four muscles forms a ribbon-like tension transmission path, with the left nasal alar cartilage as a connecter. There is also a tension thread mirrored on the right side. These two tension threads function to control the shape of both nostrils and also the morphological association between the upper lip and the nostrils.

Figure 4:
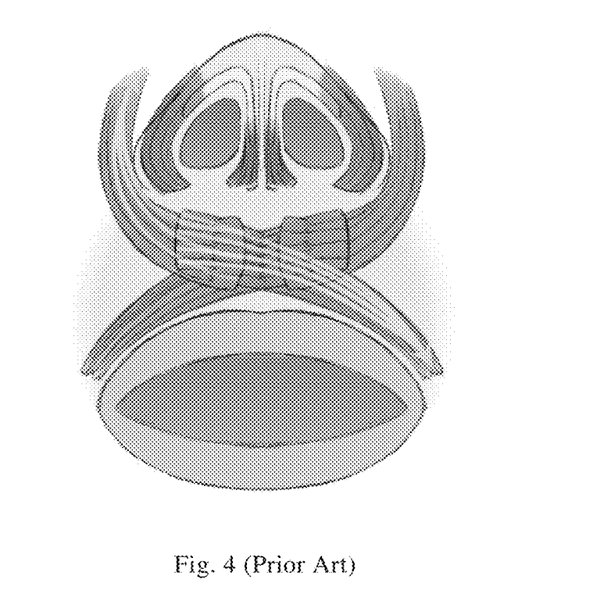
FIG. 4 is a schematic diagram of a second secondary tension thread group.

In FIG. 4, the A3 branch of orbicularis oris on the left side passes over the upper lip midline, and ends on the outer side of the right philtrum ridge; meanwhile, the B1 branch of levator labii superioris alaeque nasi on the right side bypasses the nasal ala, then interests the A3 branch of orbicularis oris on the left side, and ends at the inner margin of the right philtrum ridge. The tension of the two muscles squeezes the two slopes of the philtrum ridge, thereby uplifting the philtrum ridge. Similarly, this tension thread is also bilaterally symmetrical, forming the second secondary tension thread group.

Figure 5:
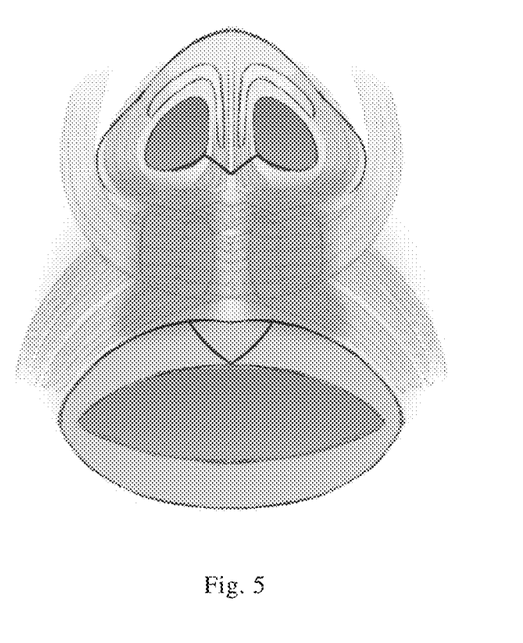
FIG. 5 is a schematic diagram of incisions and a detaching area for deepening of the philtrum.

The two blue lines in FIG. 5 refer to: (upper) an M-shaped skin incision extending along the nasal sills on both sides at the bottom of the nasal column, and (lower) a V-shaped incision in the vermilion mucosa with the two lip peaks as the apexes. The yellow highlighted area in the figure is an area in which the muscle is separated from the skin: it is up to the nasal floor on both sides, so as to expose the dilator naris muscle and the depressor septi nasi, is down to the lip arch, and extends to the nasal ala on both sides; wherein a stripe-like attachment between a part of the muscle and the skin should be retained at the central line.

Figure 6:
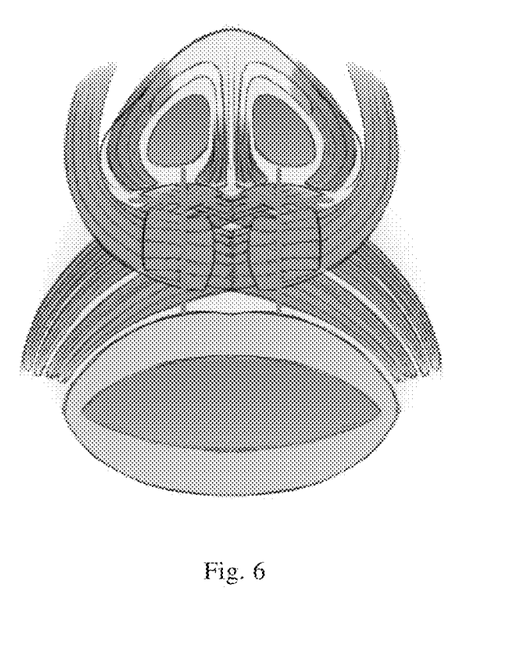
FIG. 6 is a schematic diagram of cutting lines for dividing the muscle flaps as needed for deepening of the philtrum.

In FIG. 6, after the separation of the muscle and skin is completed, the muscles are cut open longitudinally along the philtrum ridges, and then the left and right halves are further cut open transversely at ⅓ to ¼ from the top.

Figure 7:
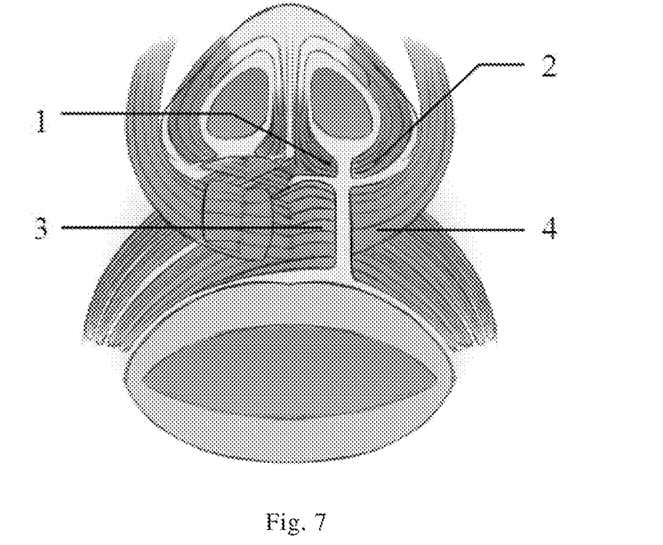
FIG. 7 is a schematic diagram of divided muscle flaps as needed for deepening of the philtrum.

In FIG. 7, after the muscles are cut open in the previous step, four muscle flaps are formed, i.e., Dilator naris muscle flap 2, Lateral orbicularis oris flap 4, Depressor septi nasi flap 1, and Medial orbicularis oris flap 3.

Figure 8:
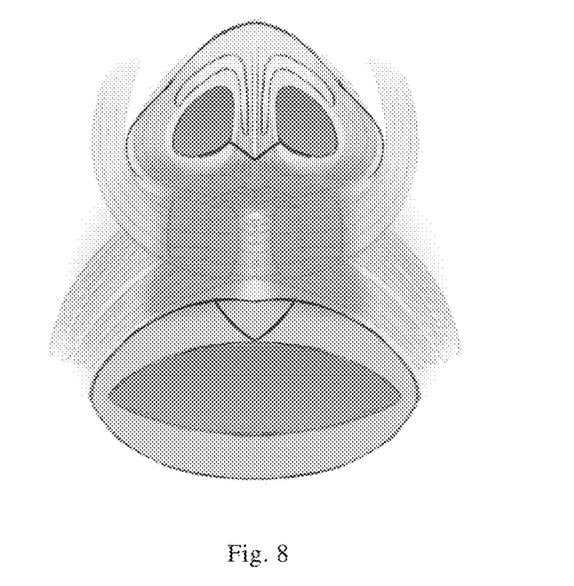
FIG. 8 is a schematic diagram of incisions and a detaching area for lengthening the philtrum.
Figure 9:
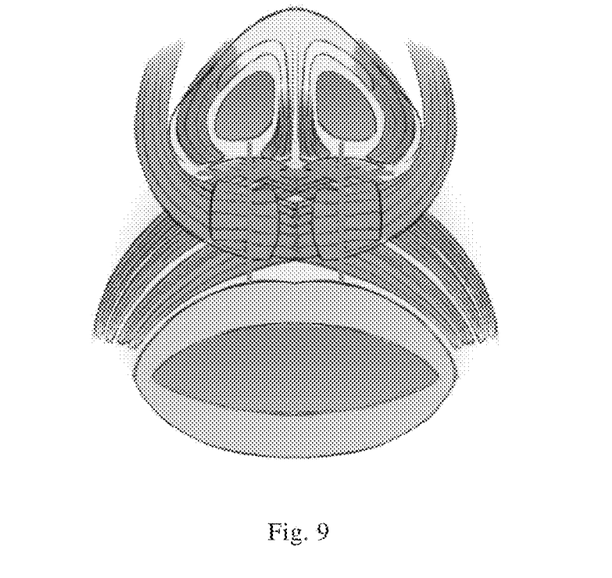
FIG. 9 is a schematic diagram of cutting lines for dividing the muscle flaps as needed for lengthening of the philtrum.
Figure 10:
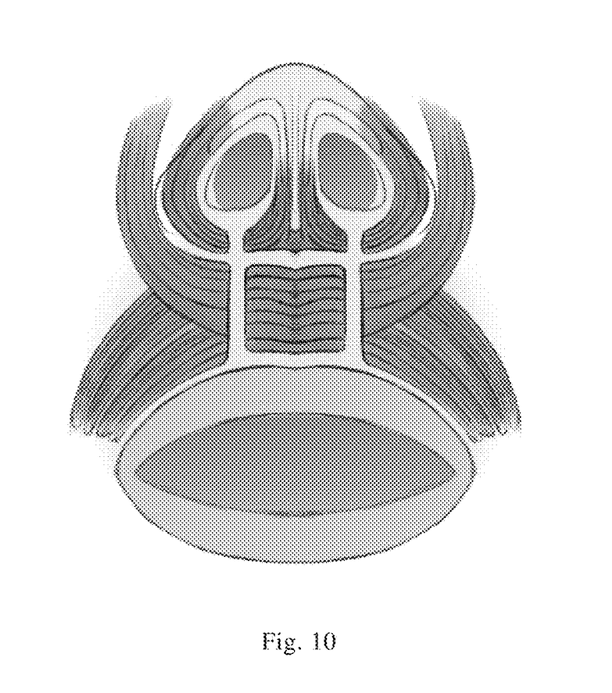
FIG. 10 is a schematic diagram of divided muscle flaps as needed for lengthening the philtrum.

FIGS. 8-10 show the incisions and the detaching area for lengthening of the philtrum, as well as the pattern for dividing the muscle flaps and the resulting muscle flaps. It differs from the mere deepening of the philtrum in that the muscle and skin at the bottom of the nasal column are separated from each other and the nasal septum is disconnected from the lower muscles.

The surgical method for reconstructing the labionasal muscle tension structure provided in accordance with the present invention has a significant effect in terms of biomechanics. Specifically, the method comprises the following steps:

1) incision: the method utilizes discreet incisions at the vermilion mucosa and at the bottom of the nasal column (the incisions are indicated by the blue lines in FIGS. 6 and 9). The incisions are advantageous in that i) incisions at the vermilion mucosa do not easily cause obvious scars; ii) skin incisions at the bottom of the nasal column can be concealed in the shadow of the nasal labial angle (the corner between the lip and the nose) and are not easily noticed.

2) formation of muscle flaps: in the central part of the upper lip (i.e., the philtrum) and at the nasal floors on both sides, the skin, muscles, and the vermilion mucosa in the incisions are sufficiently detached. For deepening of the philtrum, the detaching area is indicated by the green area in FIG. 5, but the muscle and skin located from the upper lip midline to the bottom of the nasal column are not separated from each other. For lengthening of the philtrum, as indicated by the green area in FIG. 8, the muscle and skin at the bottom of the nasal column are also separated from each other, while the subcutaneous part of the upper lip midline is not subjected to detachment.

The detached muscle layer is cut open longitudinally at the position corresponding to the philtrum ridges, to obtain two muscle flaps at the left and right. The two muscle flaps are then cut open transversely at about ¼ from the top (as indicated by the cross blue lines in FIG. 6, which are bilaterally symmetrical), to obtain four muscle flaps (as shown in FIG. 7), i.e., the depressor septi nasi flap, the dilator naris muscle flap, the medial orbicularis oris flap, and the lateral orbicularis oris flap. These four muscle flaps each mainly contain muscle fibers from the following muscles: the depressor septi nasi, the dilator naris muscle, the right orbicularis oris (the A2 and A3 branches), the left orbicularis oris (all three branches), and a part of levator labii superioris alaeque nasi (mainly the B1 branch).

For lengthening of the philtrum, the operation is the same as above, except that a connection between the orbicularis oris at the bottom of the nasal column and the depressor septi nasi should also be cut off (as shown in FIG. 9), to finally form the muscle flaps shown in FIG. 10 wherein the muscles under the philtrum are separated from the depressor septi nasi.

Subsequent surgical steps are performed symmetrically on the left and right sides, so the following descriptions and figures take the left-hand side of a human body (the right part in all the figures) as an example.

Figure 11:
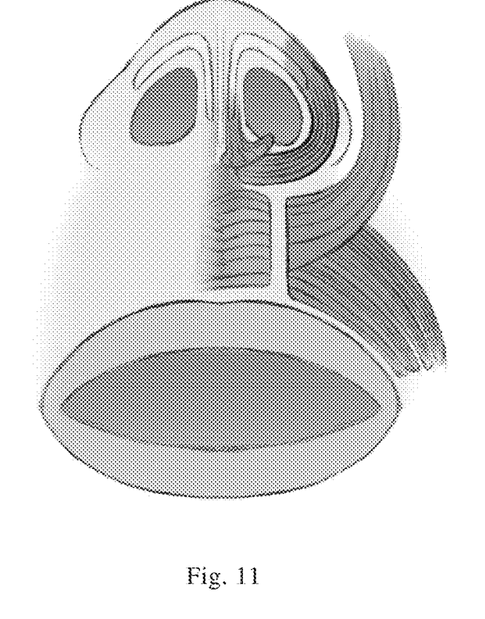
FIGS. 11-15 are schematic diagrams showing a muscle suturing process as needed for both deepening and lengthening the philtrum.
Figure 12:
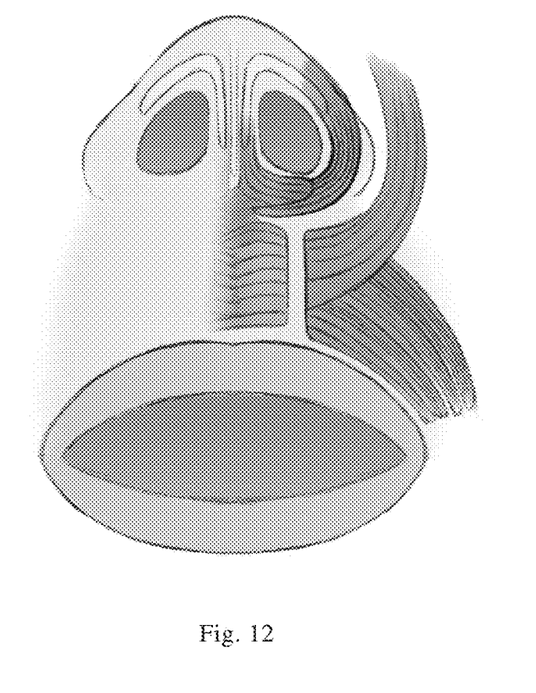
Figure 13:
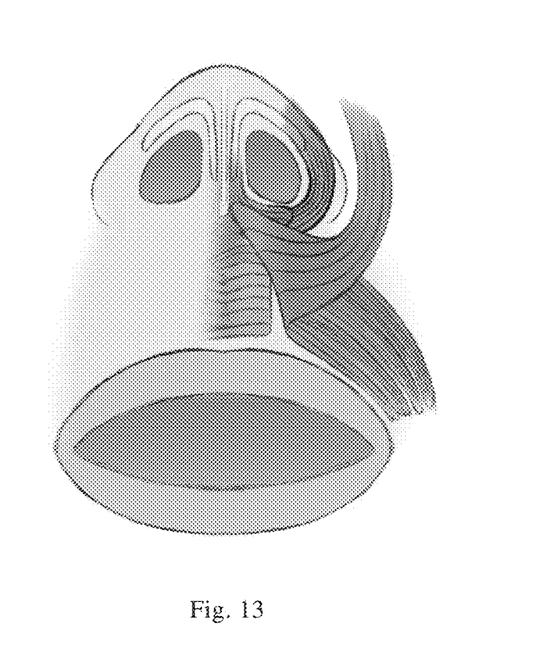
Figure 14:
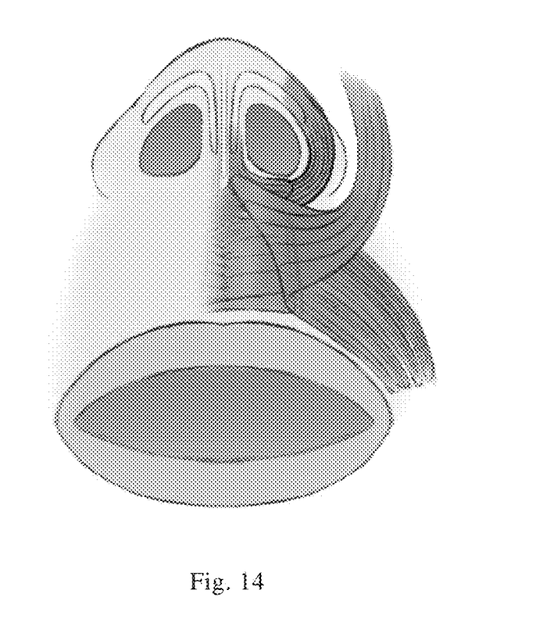
Figure 15:
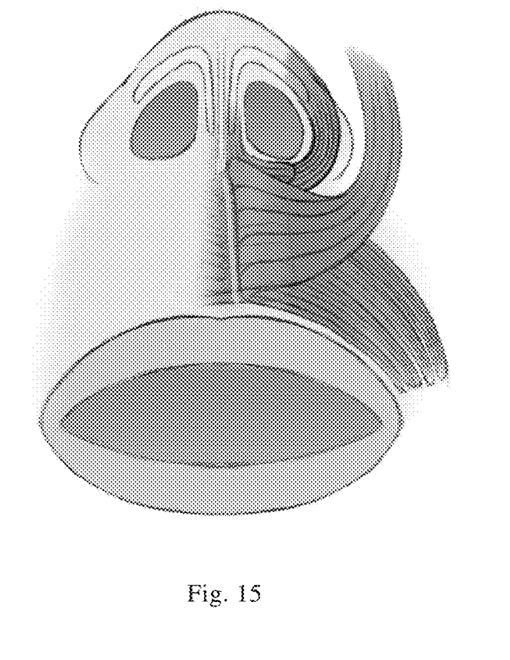
Figure 16:
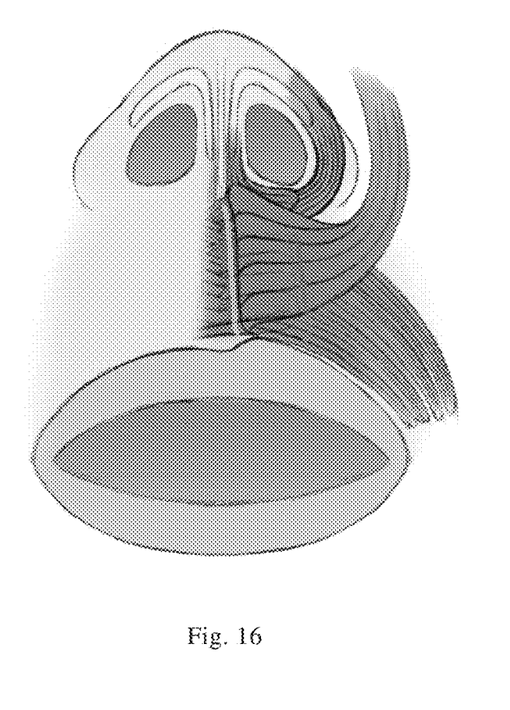
FIG. 16 is a schematic diagram showing a suturing position relationship between the medial orbicularis oris flap and the lateral orbicularis oris flap for deepening the philtrum.
Figure 17:
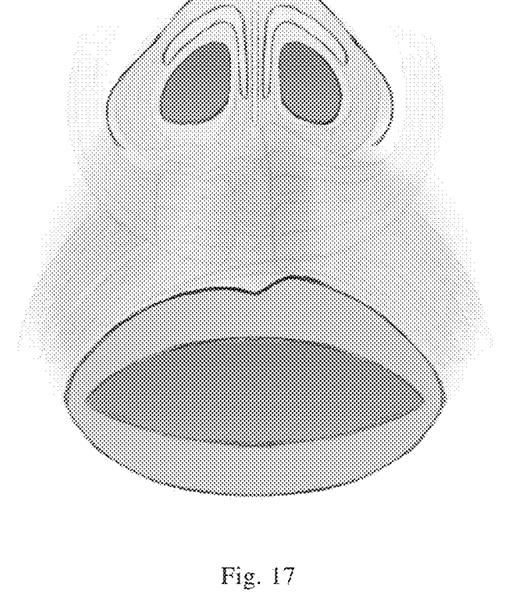
FIG. 17 is a schematic diagram showing the effect when the deepening on one side of the philtrum is completed.

3) adjustment of muscle flaps:

For both deepening and lengthening of the philtrum, the following steps should be implemented first:

i) fixing the tip of the dilator naris muscle flap to the anterior nasal spine (as shown in FIG. 11), ii) fixing the tip of the depressor septi nasi flap to the tail end of the dilator naris muscle flap (as shown in FIG. 12), and iii) lifting the tip of the lateral orbicularis oris flap inwards and upwards, and fixing the tip to the tail end of the depressor septi nasi flap (if unstable fixation is found, the suturing can be made deep into the periosteum of the anterior nasal spine or the cartilage of nasal septum for reinforcement) (as shown in FIG. 13);

4) For deepening the philtrum, the following steps are further implemented:

iv) suturing the right edge of the medial orbicularis oris flap toward the deep side of the lateral orbicularis oris flap, such that the right edge of the medial orbicularis oris flap substantially extends in the direction of a philtrum ridge (as indicated by the blue lines in FIG. 14); and v) suturing the left edge of the lateral orbicularis oris flap under the skin of the philtrum dimple, such that the left edge of the lateral orbicularis oris flap substantially extends in the direction of a philtrum ridge (as indicated by the yellow lines in FIG. 15), and at this time the edges of the medial and lateral orbicularis oris flaps are basically at the same height (as shown in FIG. 16);

Now the medial orbicularis oris flap and lateral orbicularis oris flap form a superposed structure on the surface of a human body, and their tensions acting on the skin would intersect each other under the skin of the philtrum ridges, so as to present a body surface morphology with uplifted philtrum ridges and a deepened philtrum dimple (as shown in FIG. 17, the right side of the figure is the finished morphology).

Figure 18:
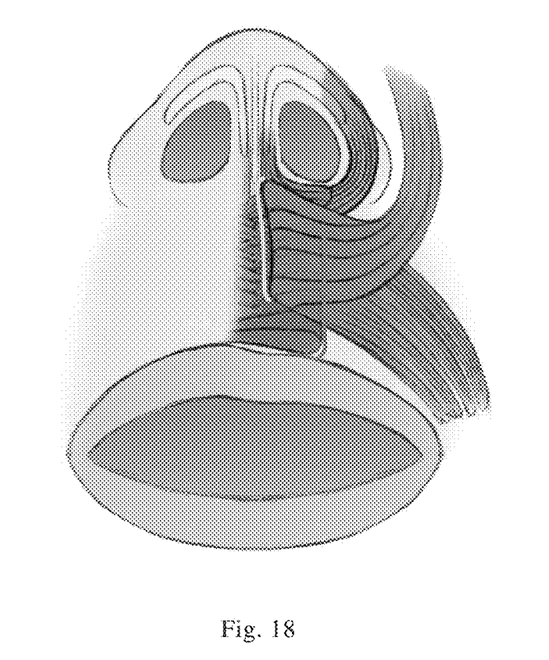
FIG. 18 is a schematic diagram showing a suturing position relationship between the medial orbicularis oris flap and the lateral orbicularis oris flap for lengthening the philtrum.

5) For lengthening the philtrum, the operations in steps iv) and v) are slightly changed as follows:

vi) being substantially the same as steps iv) and v), lifting the tip of the lateral orbicularis oris flap inwards and upwards, fixing the tip to the anterior nasal spine, and sequentially suturing the medial orbicularis oris flap and lateral orbicularis oris flap to reconstruct the morphology of the philtrum however, as different from steps iv) and v), according to how much the philtrum needs to be lengthened, the fixing position of the lower edge of the lateral orbicularis oris flap is correspondingly made higher to make the muscle flap obliquely inwards and upwards, while the medial orbicularis oris flap is correspondingly made lower, so as to make the two muscle flaps obliquely misaligned with each other. That is, the more the philtrum needs to be lengthened, the greater the misalignment of the sutured two muscle flaps is made (as shown in FIG. 18).

Figure 19:
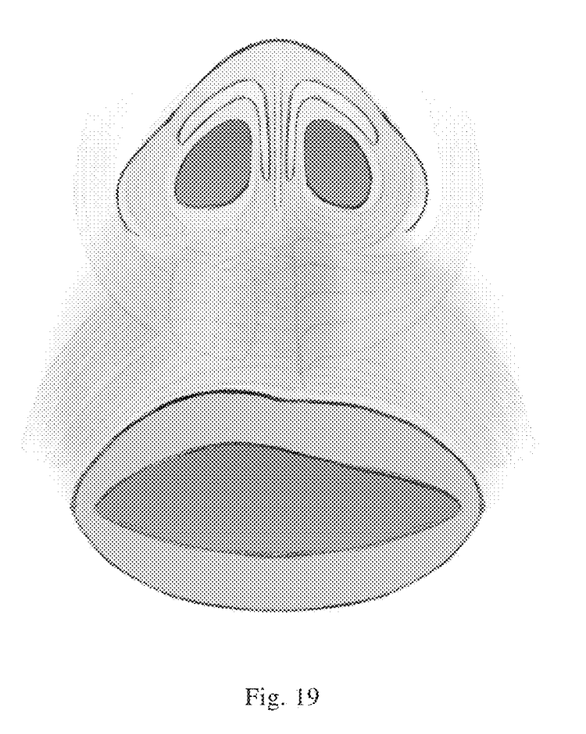
FIG. 19 is a schematic diagram showing the effect when the lengthening on one side of the philtrum is completed.

At this time, the lateral orbicularis oris pulls the middle of the upper lip downwards by a tension acting obliquely outwards and downwards, thereby entirely lowering the upper lip, and presenting an effect of a lengthened philtrum (as shown in FIG. 19).

In the process of deepening the philtrum, we fully detach the muscle fibers of the dilator naris muscle originally attached to the edge of the anterior nasal aperture, to form the dilator naris muscle flap, which is fixed on the anterior nasal spine and connected to the depressor septi nasi flap. Due to the pulling of these two, the nasal ala is drawn inwards, reducing the nostril width. At the same time, the peripheral tissue of the upper lip is also thus gathered toward the middle, to provide available skin for subsequent steps. Fixing the tip of the lateral orbicularis oris flap to the anterior nasal spine further enhances this effect, and also raises the nasal floor. When the lateral orbicularis oris flap is also simultaneously combined with the medial orbicularis oris flap under the skin of the philtrum ridges, the muscle tensions of both intersect under the philtrum ridges, and uplifting of the philtrum ridges and depression of the philtrum dimple are naturally realized under the dual action of muscle tensions and tissue gathering. The morphology of the obtained philtrum is more in line with the normal muscle tension structure due to the muscle tension, and therefore has a more natural and aesthetic appearance.

As described above, in the philtrum lengthening surgery, after the dilator naris muscle flap and the depressor septi nasi flap are connected, the lateral orbicularis oris flap is misaligned with the medial orbicularis oris flap in terms of the height after suturing, so that the lateral orbicularis oris flap exerts a tension acting obliquely outwards and downwards. Such tensions from both the left and right sides form a downward combined force and pull the upper lip entirely downwards. As a result, the middle of the upper lip, i.e., the philtrum, appears lengthened.

Example 1: Philtrum Lengthening Surgery

Figure 20:
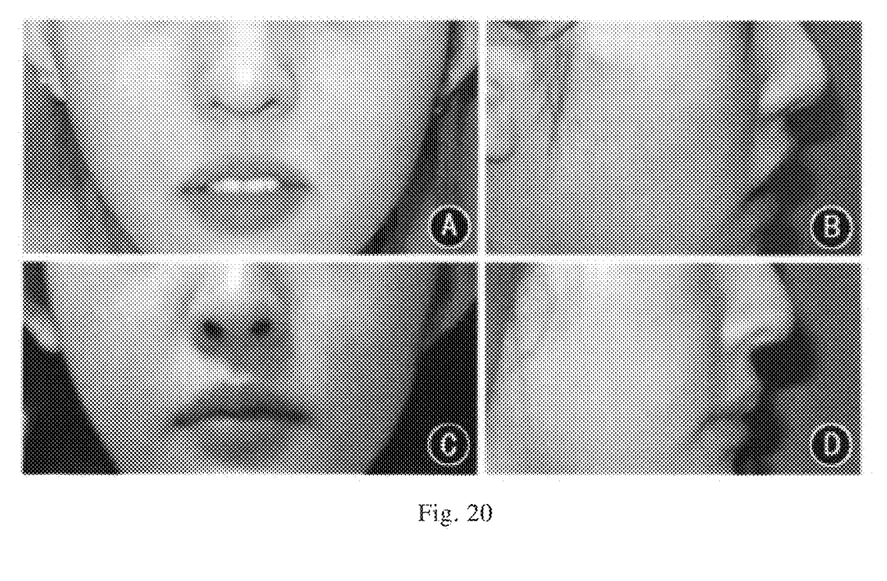
FIG. 20 shows photos for comparison before and after the surgery in Example 1.

A 20-year-old female patient was subjected to a surgical method for reconstructing a labionasal muscle tension structure provided in accordance with the present invention, and achieved a remarkable repairing effect. The details can be seen in FIG. 20, in which A and B present situations before the surgery, and C and D present situations 1 year after the surgery. One year after the surgery, the lip showed a clear profile, and the upper lip was lengthened.

Example 2: Philtrum Deepening Surgery

Figure 21:
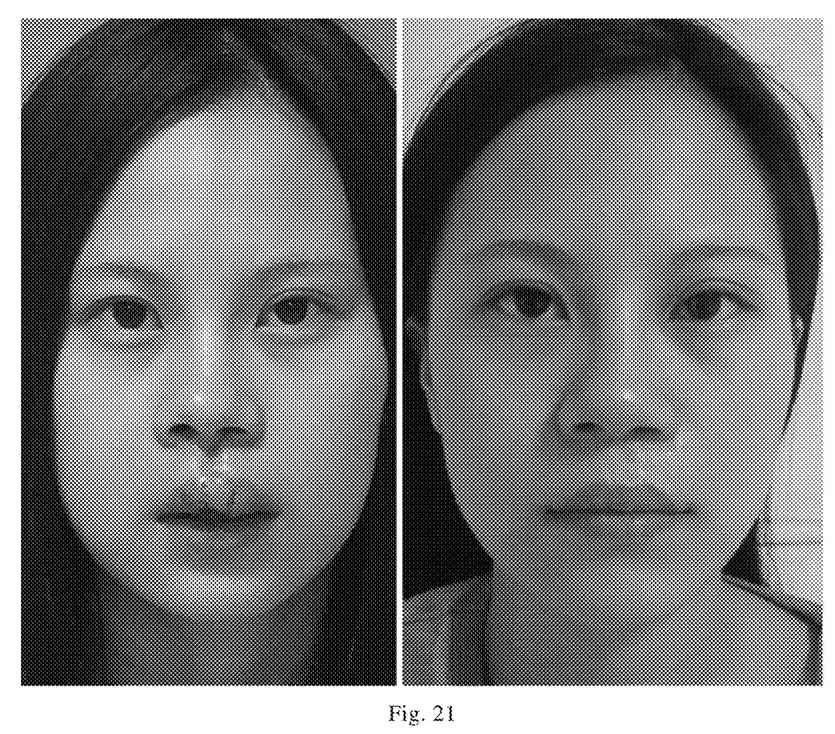
FIG. 21 shows photos for comparison before and after the surgery in Example 2.

A 25-year-old female patient, who had a short, blunt, and poorly shaped upper lip which was open to leave the teeth exposed, was subjected to a surgical method for reconstructing a labionasal muscle tension structure provided in accordance with the present invention, and achieved a remarkable repairing effect. The details can be seen in FIG. 21, in which the left panel presents a situation before the surgery, and the right panel presents a situation 1 year after the surgery. One year after the surgery, the lip showed a clear profile, and the upper lip was deepened.

Example 3: Philtrum Lengthening Surgery

Figure 22:
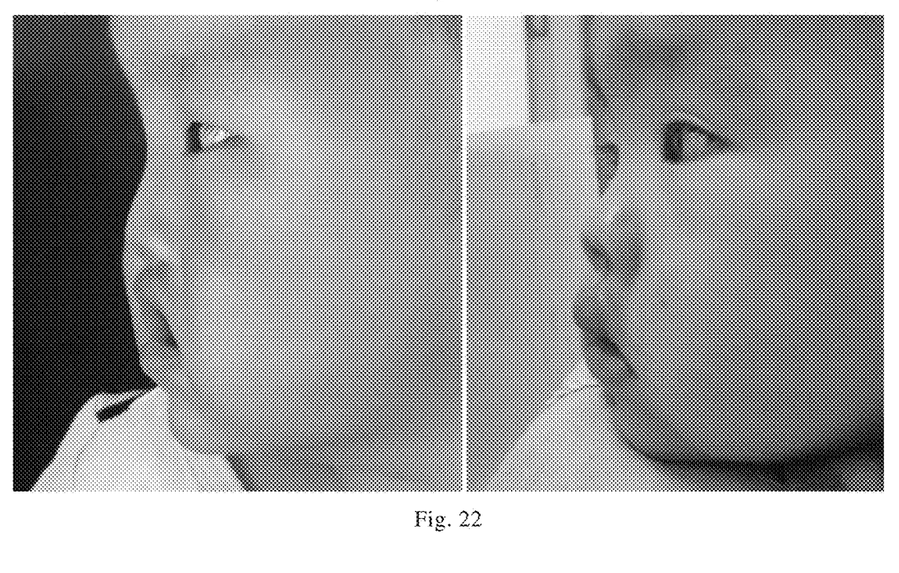
FIG. 22 shows photos for comparison before and after the surgery in Example 3.

A 2-year-old male patient, who had a short, blunt, and poorly shaped upper lip which was open to leave the teeth exposed, was subjected to a surgical method for reconstructing a labionasal muscle tension structure provided in accordance with the present invention, and achieved a remarkable repairing effect. The details can be seen in FIG. 22, in which the left panel presents a situation before the surgery, and the right panel presents a situation 1 year after the surgery. One year after the surgery, the lip showed a clear profile, and the upper lip was lengthened.

The technical problem to be solved by the present invention is to design a cosmetic surgical method for presenting a deeper or longer philtrum at the lip by adjusting muscle flaps at the lips and nose. The theoretical basis of this surgical method is a "theory of labionasal muscle tension thread group" summarized from a series of studies with respect to anatomy, biomechanics and clinical surgical verification. This theory proposes an anatomical concept "labionasal muscle complex" and a biomechanical concept "labionasal muscle tension thread groups", and ascribes the formation of the surface morphology of lips and nose to the relationship between tensions of labionasal muscles. According to this theory, the labionasal muscle tension structure can be reconstructed by surgical adjustment of the position and direction of the muscle flaps, so as to allow the lips and nose to reach a new biomechanical balance, and to produce an effect of changing the morphology of the lips and nose.

The above description only refers to preferred examples of the present invention, and does not limit the present invention. Any modifications, equivalents, improvements and the like made within the spirit and principle of the present invention are included in the scope of protection of the present invention.

The invention claimed is:

1. A surgical method for reconstructing a labionasal muscle tension structure, comprising the steps of:
   1) incision: making incisions at vermilion mucosa and at the bottom of a nasal column;
   2) formation of muscle flaps: detaching a muscle layer in the incision from a skin and the vermilion mucosa, and cutting open the detached muscle layer both longitudinally at the positions corresponding to philtrum ridges and transversely at about ¼ from the top, to obtain four muscle flaps which are respectively a depressor septi nasi flap, a dilator naris muscle flap, a medial orbicularis oris flap, and a lateral orbicularis oris flap;

3) adjustment of muscle flaps: fixing the tip of the dilator naris muscle flap to the anterior nasal spine, fixing the tip of the depressor septi nasi flap to the tail end of the dilator naris muscle flap, and then cross-stitching the lateral orbicularis oris flap and the medial orbicularis oris flap to deepen and/or lengthen the philtrum; and 4) suturing: after the muscle flaps are treated, suturing the two incisions at the vermilion mucosa and the bottom of the nasal column as they were.

2. The surgical method for reconstructing a labionasal muscle tension structure according to claim 1, wherein in the step of detaching the muscle layer in the incision from the skin and the vermilion mucosa, when the philtrum is to be deepened, the muscle located from the upper lip midline to the bottom of the nasal column is not separated from the skin.

3. The surgical method for reconstructing a labionasal muscle tension structure according to claim 1, wherein in the step of detaching the muscle layer in the incision from the skin and the vermilion mucosa, when the philtrum is to be lengthened, the muscle at the bottom of the nasal column is separated from the skin, while the subcutaneous portion of the upper lip midline is not separated.

4. The surgical method for reconstructing a labionasal muscle tension structure according to claim 1, wherein the deepening the philtrum comprises: lifting the tip of the lateral orbicularis oris flap inwards and upwards, and fixing the tip to the tail end of the depressor septi nasi flap; suturing the right edge of the medial orbicularis oris flap toward the deep side of the lateral orbicularis oris flap, such that the right edge of the medial orbicularis oris flap substantially extends generally in the direction of a philtrum ridge; and suturing the left edge of the lateral orbicularis oris flap under the skin of the philtrum dimple, such that the left edge of the lateral orbicularis oris flap substantially extends in the direction of a philtrum ridge.

5. The surgical method for reconstructing a labionasal muscle tension structure according to claim 1, wherein lengthening the philtrum comprises: lifting the tip of the lateral orbicularis oris flap inwards and upwards, and fixing the tip to the anterior nasal spine; and suturing the right edge of the medial orbicularis oris flap toward the deep side of the lateral orbicularis oris flap, and suturing the left edge of the lateral orbicularis oris flap under the skin of the philtrum dimple, such that when the suturing the lateral orbicularis oris flap is sutured relatively high and the medial orbicularis oris flap is relatively low, and the height difference between the lateral orbicularis oris flap and the medial orbicularis oris flap makes the philtrum lengthened.

* * * * *